US00PP30653P3

(12) United States Plant Patent
Engelke et al.

(10) Patent No.: US PP30,653 P3
(45) Date of Patent: Jul. 2, 2019

(54) ZOYSIAGRASS PLANT NAMED 'DALZ 0102'

(50) Latin Name: ***Zoysia japonica* Steud.**
Varietal Denomination: DALZ 0102

(71) Applicant: The Texas A&M University System, College Station, TX (US)

(72) Inventors: Milton C. Engelke, College Station, TX (US); Anthony D. Genovesi, Dallas, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/731,369

(22) Filed: Jun. 2, 2017

(65) Prior Publication Data

US 2018/0352713 P1 Dec. 6, 2018

(51) Int. Cl.
*A01H 5/12* (2018.01)
*A01H 6/46* (2018.01)

(52) U.S. Cl.
USPC ..... Plt./390
CPC ..... *A01H 6/469* (2018.05)

(58) Field of Classification Search
USPC ..... Plt./390
See application file for complete search history.

(56) References Cited

U.S. PATENT DOCUMENTS

| | | | |
|---|---|---|---|
| PP11,515 | P | 9/2000 | Engelke |
| PP13,166 | P2 | 11/2002 | Doguet |
| PP13,178 | P2 | 11/2002 | Doguet |
| PP14,130 | P2 | 9/2003 | Engelke et al. |

OTHER PUBLICATIONS

"Freezing Tolerance and Seasonal Color of Experimental Zoysiagrasses," Okeyo et al., Crop Science, vol. 51, Nov.-Dec. 2011, www.crops.org, pp. 2858-2863.*
"Gene Banks Offer Breeders Acess to Germplasm," Widrlechner et al, May 5, 2008, http://www.nurseymag.com/article/gene-banks-offer-breeders-access-to-germplasm/.*
"Registration of 'Chisolm' Zoysiagrass," Chandra et al.,Journal of Plant Registrations Abstract, https://dl.sciencesocieties.org/publications/jpr/abstracts/9/1/21, vol. 9, No. 1, p. 21-26, published Oct. 10, 2014.*
"Plant Germplasm Report—Collection of Low-Maintenance Turf Germplasm and Seed/Scientific Exchange with China", Johnson et al, https://www.ars.usda.gov/arsuserfiles/20801000/china06.pdf, 2006.*
"Stolon Growth Characteristics and Establishment Rates of Zosiagrass Progeny," Okeyo et al, HortScience 46(1):113-117. 2011.*
"Zoysiagrass Genotypes Differ in Susceptibility to the Bluegrass Billbug, Aphenophorus parvulus," Fry and Cloyd, HortScience vol. 46(9) Sep. 2011, pp. 1314-1316.*
Fry et al., "Zoysiagrass genotypes differ in susceptibility to the bluegrass billbug, *Sphenophorus parvulus*," *HortScience* 46:1314-1316; 2011.
Grau et al., "'Meyer' (Z-52) zoysiagrass," USGA J. of Turf Management 4(6):30-31; 1951.
National Turfgrass Evaluation Program, "National zoysiagrass test—2002. Final Report No. 07-11. (ntep.org)," 2007.
Obasa et al., "Susceptibility of zoysiagrass germplasm to large patch caused by *Rhizoctonia solani*," *HortScience* 47:1252-1256; 2012.
Okeyo et al., "Stolon growth characteristics and establishment rates of zoysiagrass progeny," *HortScience* 46:113-117; 2011.
Okeyo et al., "Freezing tolerance and seasonal color of experimental zoysiagrasses," *Crop Sci* 51: 2858-2863; 2011.
Patton et al., "Zoysiagrass species and genotypes differ in their winter injury and freeze tolerance," *Crop Sci* 47:1619-1627; 2007.
Patton et al., "Stolon growth and dry matter partitioning explain differences in zoysiagrass establishment rates," *Crop Sci* 47:1237-1245; 2007.
Reinert et al., "Zoysiagrass resistance to the zoysiagrass mite, *Eriophyes zoysiae* (Acari:*Eriopyidae*)," *Int Turfgrass Soc Res J* 7:349-352; 1993.
Wherley et al., "Low-input performance of zoysiagrass (*Zoysia* spp.) cultivars maintained under dense tree shade," HortScience 46:1033-1037; 2011.
Zhang et al., "Preliminary evaluation of freezing tolerance of Meyer and DALZ 0102 zoysiagrass," Kansas State Turfgrass Research. Report of Progress 981. KSU Agricultural Experiment Station and Cooperative Extension Service, pp. 65-70; 2007.

* cited by examiner

*Primary Examiner* — Anne Marie Grunberg
(74) *Attorney, Agent, or Firm* — Dentons US LLP

(57) ABSTRACT

'DALZ 0102' is a new variety of zoysiagrass distinguished by having superior turf quality, rapid rate of establishment, rapid recovery rate following damage, comparable cold hardiness, good shade tolerance, good fall color retention, high shoot density, low seedhead number, good resistance to bluegrass billbug, excellent resistance to zoysiagrass mite, good resistance to dollar spot, and good resistance to take-all patch, as disclosed herein.

2 Drawing Sheets

ZOYSIAGRASS PLANT NAMED 'DALZ 0102'

Latin name of the genus and species of the plant claimed: *Zoysia japonica* Steud.

Cultivar denomination: 'DALZ 0102'.

STATEMENT REGARDING FEDERALLY SPONSORED RESEARCH

Not applicable.

BACKGROUND OF THE INVENTION

Zoysiagrasses (*Zoysia* spp.) are in a genus of warm-season, C4 monocots native to Pacific Rim countries with climatic extensions of up to 50° latitude. Among the 11 zoysiagrass species identified, three have been grown as turfgrasses in the United States since the 1930s: Japanese Lawngrass (*Z. japonica* Steud.), Manilagrass [*Z. matrella* (L.) Merr.], and Mascarenegrass [*Z. pacifica* (Goudsw.) M. Hotta & Kuroi] (Halsey, 1956; Engelke and Anderson, 2003). These three species are collectively referred to as zoysiagrass. The somatic chromosome number for the genera is uniformly 2n=4x=40 (Forbes, 1952, Yaneshita et al., 1999). Zoysiagrass cultivars readily cross with other grasses within the species, as well as other species within the genus (Forbes, 1952; Hong and Yeam, 1985). Speciation primarily is attributed to geographic distribution and floral nicking.

Zoysiagrass is recognized for its tolerance to heat and salt, pest resistance, and low maintenance requirements (Fry and Huang, 2004). For adaptation in the upper south and middle portions of the United States, freezing tolerance is a limiting factor. The transition zone for turfgrass adaptation can be characterized as a unique region bordered on the north from Maryland through eastern Kansas. The southern borders of North Carolina and Tennessee (Dunn and Diesburg, 2004) define the southern extent of the region. Whether or not a particular warm-season turfgrass species or cultivar will perform well in the transition zone is usually determined by its ability to persist through the coldest of winters.

Since the release of 'Meyer' in 1952 (unpatented, Grau and Radko, 1951), it has been the principal cultivar used in the transition zone, primarily because of its excellent freezing tolerance. However, it has slow establishment and recuperative rates (Fry and Dernoeden, 1987), relatively shallow rooting depth and below-average drought avoidance capability (Marcum et al., 1995), and is susceptible to some pests, including the fungal disease large patch (*Rhizoctonia solani* Kühn) (Green et al., 1993) and zoysiagrass mite (*Eriophyes zoysiae* Baker, Kono, and O'Neill) (Reinert et al., 1993).

The invention relates to a new and distinct cultivar of zoysiagrass named 'DALZ 0102' with unknown parentage. 'DALZ 0102' is a clonal selection made from a germplasm nursery established in Dallas, Tex. 'DALZ 0102' was originally evaluated under the designation TAES 4436. 'DALZ 0102' was evaluated at 17 distinct locations in 16 states. Plugs measuring 4 $cm^2$ were planted on 30 cm centers at each site in plots measuring 1.5 $m^2$.

'DALZ 0102' is a medium-coarse textured, highly rhizomatous, vegetatively propagated clone of a *Z. japonica* seedling with excellent turf quality, comparable cold hardiness to 'Meyer' as well as superior establishment rate and recuperative ability to that of 'Meyer'. 'DALZ 0102' is suitable for use as a warm season turfgrass for residential and commercial lawns, parks, and golf courses in the transition zone of the United States in sunny or moderately shaded areas where turf quality, rapid spread, coupled with cold hardiness are desired.

'DALZ 0102' has not been made publicly available more than one year prior to the filing date of this application.

SUMMARY OF THE INVENTION

The following are the most outstanding and distinguishing characteristics of 'DALZ 0102'. (1) 'DALZ 0102' has superior turf quality relative to other *Zoysia japonica* cultivars adapted to the transition zone; (2) 'DALZ 0102' exhibits a rapid rate of establishment; (3) 'DALZ 0102' exhibits a rapid recovery rate following damage; (4) 'DALZ 0102' exhibits comparable cold hardiness relative to other *Zoysia japonica* cultivars adapted to the transition zone; (5) 'DALZ 0102' exhibits good shade tolerance; (6) 'DALZ 0102' exhibits good fall color retention; (7) 'DALZ 0102' exhibits high shoot density; (8) 'DALZ 0102' exhibits low seedhead number; (9) 'DALZ 0102' exhibits good resistance to bluegrass billbug; (10) 'DALZ 0102' exhibits excellent resistance to zoysiagrass mite; (11) 'DALZ 0102' exhibits good resistance to dollar spot; and (12) 'DALZ 0102' exhibits good resistance to take-all patch. Multi-location and multi-year field evaluation showed 'DALZ 0102' to exhibit excellent turf quality, comparable cold hardiness to 'Meyer' as well as superior establishment rate and recuperative ability to that of 'Meyer'. 'DALZ 0102' is suitable for use as a warm season turfgrass for residential and commercial lawns, parks, and golf courses in the transition zone of the United States in sunny or moderately shaded areas where turf quality, rapid spread, coupled with cold hardiness are desired.

BRIEF DESCRIPTION OF THE DRAWINGS

This new zoysiagrass variety is illustrated by the accompanying photographs. The colors shown are as true as can be reasonably obtained by conventional photographic procedures.

DETAILED BOTANICAL DESCRIPTION

Figure 1:
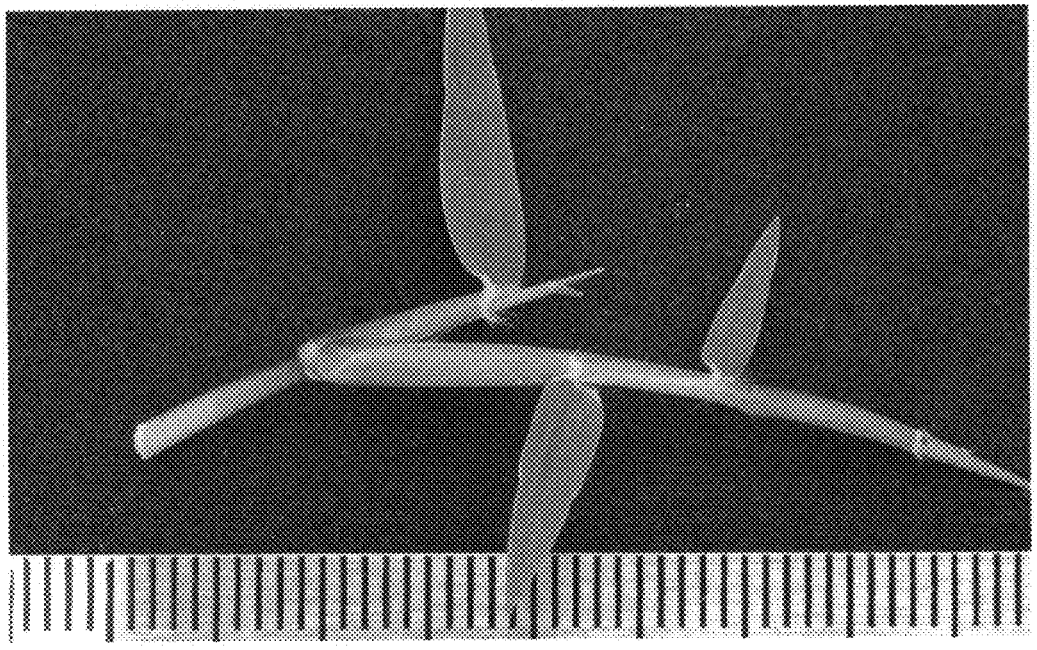
FIG. 1—Stolon, node and leaf color and orientation of 'DALZ 0102'. Photo represents very young leaves on the growing tip of a developing stolon.
Figure 2:
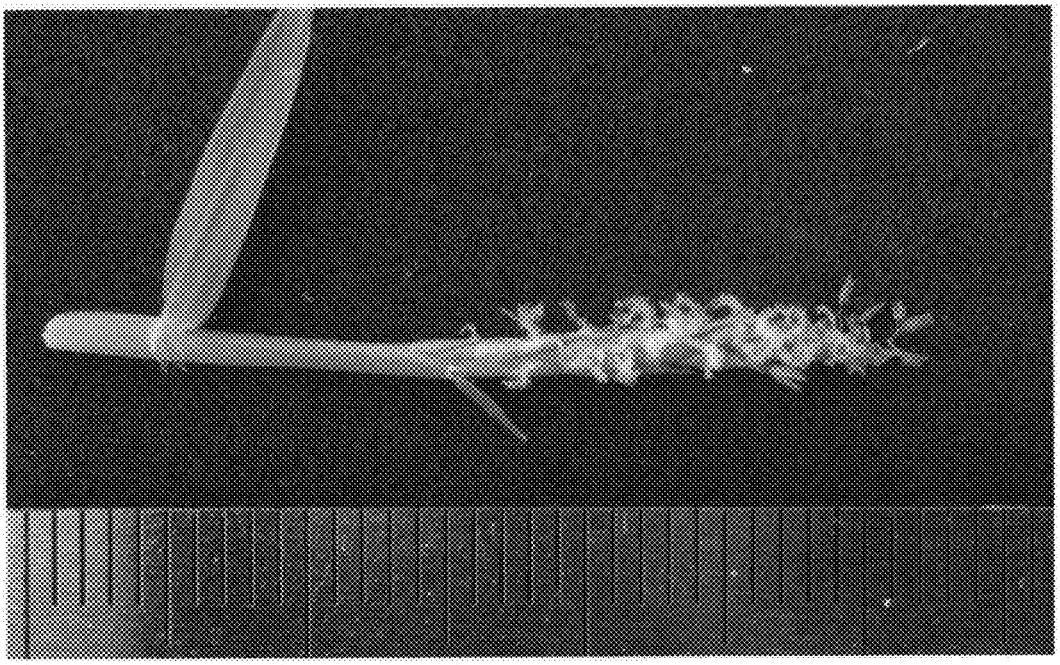
FIG. 2—Inflorescence of 'DALZ 0102' during anthesis. Evidence of protogyny with female stigmas exerted prior to anther exertion. Floral development progresses from apex to the peduncle and generally anthesis lags by 3-5 days behind stigma receptivity.

The following detailed description sets forth the distinctive characteristics of Zoysiagrass variety 'DALZ 0102'. Color references are to The R.H.S. Colour Chart of The Royal Horticultural Society of London (R.H.S.), 2007 5th Edition. Version 2, unless otherwise indicated. If any R.H.S. color designations below differ from the accompanying photographs, the R.H.S. color designations are accurate.

Plant length: Managed plots are maintained a 1.5" (38.1 mm) or if unmanaged 3.87" (98.3 mm).

Vegetative growth habit: Rhizomatous, mat-forming perennial.

Attitude of tillers on the culm: Growing from nodes at 45 degree angle.

Basal leaf sheath anthocyanin coloration: Purple (70A).

Leaf sheath pubescence: Absent to sparse.

Leaf buds: Rolled.

Leaf blades: Green (N134C).
Time of flowering: Spring and fall.
Self-fertility of flowers: Poorly self-fertile.
Glume:
*Length.*—25 mm.
*Anthocyanin coloration.*—Absent.
*Coloration when newly emerged from the boot.*—Pale green (134D).
*Coloration when pollinated on spikelets.*—Anthocyanin develops with age toward the distal end, purple (64A).
Number of bristles in the glume: 0.
Bristle length and density:
Culm:
*Diameter.*—2.16 mm.
*Node anthocyanin coloration.*—Purple (70A).
*Node pubescence.*—Absent.
*Internode anthocyanin coloration.*—Green (134D).
*Number of panicle-bearing tillers.*—1.
Panicle:
*Diameter.*—2.8 mm.
*Shape.*—Cylindric.
*Length of the main rachis.*—25 mm.
Caryopsis:
*Shape.*—Elliptic.
*Coloration.*—Brown (164A).
Auricles: Present.
Ligules: Present.
Ligule hairs: Present.
Collars: Present.
Rhizomes: Present.
Stolons: Present.
Anthers: Present, with tinge of anthocyanin.
*Coloration.*—Pink (38A).
Stigmas: Present.
*Coloration.*—White (NN155D).

Origin—'DALZ 0102' originated from a population of more than 150 *Z. japonica* plant introductions collected from managed turf sites throughout the Pacific Rim. This collection was evaluated under field conditions in Dallas Tex. The initial plot identity was lost in Dallas following two winters. The few surviving genotypes spread to fill the neighboring plots which were bare and were allowed to grow and fill the entire area of these colonized plots. Therefore, genotype identity of these surviving genotypes was lost and they likely colonized the neighboring plots from a sparse number of sprigs or from volunteer seed. Sixteen plugs were selected from these field plots with one plug coded as TAES 4436, which was evaluated in a replicated field trial planted in Dallas, Tex. Based on its promising performance, it was coded as 'DALZ 0102' and entered in a National Turfgrass Evaluation Program Zoysiagrass Test (NTEP).

'DALZ 0102' was first asexually vegetatively propagated in Dallas, Tex., in 1999, and has remained true to type following propagation.

Morphological comparisons reported herein were obtained from a greenhouse study conducted in Dallas, Tex., using 3.8 L pots each of 'DALZ 0102', 'JaMur' (*Z. japonica*; U.S. Plant Pat. No. 13,178), 'Palisades' (*Z. japonica*; U.S. Plant Pat. No. 11,515), 'Zeon' (*Z. matrella*; U.S. Plant Pat. No. 13,166), and 'Zorro' (*Z. matrella*; U.S. Plant Pat. No. 14,130) arranged in a randomized complete block design with 10 replications (Table 1). Leaf blade length was determined for the three tallest leaves in each of the 10 replicates of all five entries by measuring the distance between the base and the tip of the leaf. Leaf blade width was recorded 15 mm above the collar for the same three tallest leaves. Internode length and diameter between the fourth and fifth nodes, and node diameter of the fourth node were measured for three longest stolons in each pot.

Data were collected for leaf texture, establishment rate and recovery from divot (Table 2), turfgrass quality (Table 3), fall color (Table 4), spring and fall density (Table 5), and susceptibility to diseases based on NTEP guidelines (Morris and Shearman, 1999). Additional data are discussed for responses to freezing tolerance following methods described by Patton and Reicher (2007) and Zhang and Fry (2007), and for response to shade following methods described by Wherley et al. (2011). Seedhead production data (Table 6) were based on NTEP guidelines (Morris and Shearman, 1999).

Morphology, Establishment and Quality—The overall mean ratings based on visual assessment of leaf texture in the NTEP test indicated that 'DALZ 0102' had a coarser texture than 'Meyer', the standard cultivar used in the transition zone, at 8 of 13 locations but not significantly different at the other five locations. In the morphological study conducted in Dallas, Tex., 'DALZ 0102' exhibited longer ($p<0.05$) and wider leaves, longer internode lengths and stolon nodes with greater diameter than the *Z. matrella* cultivars, 'Zeon' and 'Zorro' (Table 1). 'DALZ 0102' had intermediate leaf blade lengths and widths compared to those of 'JaMur' and 'Palisades'. Similarly, 'DALZ 0102' was intermediate to 'JaMur' and 'Palisades' for internode length, and node diameter. The internode diameter of 'DALZ 0102' was found to be similar to 'Palisades' and 'JaMur' and larger than 'Zorro'.

TABLE 1

Comparison of morphological traits for 'DALZ 0102' and commercial zoysiagrass cultivars evaluated in a greenhouse study in Dallas, TX.

| Cultivar | Blade length (mm)† | Blade width (mm)‡ | Internode length (mm)§ | Internode diameter (mm) | Node diameter (mm) |
|---|---|---|---|---|---|
| 'JaMur' | 72.3 c¶ | 3.7 a | 14.1 c | 2.0 a | 3.0 a |
| 'Palisades' | 109.0 a | 3.3 c | 15.9 b | 2.0 a | 2.9 ab |
| 'Zeon' | 50.2 e | 2.1 d | 19.5 a | 2.0 a | 2.5 c |
| 'Zorro' | 68.2 d | 1.5 e | 17.8 a | 1.5 b | 2.0 d |
| 'DALZ 0102' | 98.3 b | 3.5 b | 15.8 b c | 2.2 a | 2.8 b |

†Leaf blade length was determined by measuring the distance between the base and the tip of three tallest leaves in each of the ten replicate pots. Numbers represent the mean of 30 measurements.
‡Leaf blade width was recorded 15 mm above the leaf collar for three tallest leaves in each of the ten replicate pots. Numbers represent the mean of 30 measurements.
§Internode length and diameter were measured between the 4th and 5th node for three longest stolons in each of the ten replicate pots. Node diameter was measured for the 4th node. Internode length and diameter and node diameter are a mean of at least 30 measurements.
¶Means in a column followed by the same letter(s) are not significantly different according to Fisher's Protected LSD Test ($p \leq 0.05$).

Stolon growth characteristics and their influence on establishment rate were evaluated in KS and IN where both 'DALZ 0102' and 'Meyer' were included (Okeyo et al., 2011a; Patton et al., 2007). In Manhattan, Kans., 'DALZ 0102' and 'Meyer' were similar in separate experiments over two summers in rates of stolon initiation, elongation, and branching. 'DALZ 0102' also had the same level of plot coverage (94.7%) as 'Meyer' after planting plugs in June, 2007. In the second summer (2008), however, coverage of 'DALZ 0102' (90%) was superior to that of 'Meyer' (50%) in September after planting in June (Okeyo et al., 2011a). In Indiana, 'DALZ 0102' had greater mean and total stolon lengths than 'Meyer' at 43 days after planting (Patton et al., 2007). In addition, 'DALZ 0102' was superior to 'Meyer'

($p<0.05$) in coverage at 59 (889 $cm^2$ vs. 400 $cm^2$ of ground cover) and 91 (3450 $cm^2$ vs. 1203 $cm^2$ of ground cover) days after planting, 'Meyer' also had a slower stolon elongation rate (5.0 mm $day^{-1}$) compared to 'DALZ 0102' (7.7 mm $day^{-1}$).

Establishment rates were evaluated at most NTEP locations. Establishment was significantly faster for 'DALZ 0102' than 'Meyer' in Lexington, Ky.; Florence, S.C.; College Station, Tex.; West Lafayette, Ind. and Stillwater, Okla. (Table 2). Establishment rate for 'DALZ 0102' was in the same statistical group as 'Meyer' in Jay, Fla., Mississippi State, Miss. and Raleigh, N.C. Divots refer to the pieces of sod that are scraped from the surface of golf course fairways and tees when a golf ball is hit with a golf club while swinging. In the NTEP, 'DALZ 0102' exhibited a divot recovery level of 85%, which was superior ($p<0.05$) to that of 'Meyer' (52%).

TABLE 2

Establishment and divot recovery of vegetatively propagated zoysiagrasses in the NTEP Test over five years.

| | Divot Recovery (%)† | Establishment (%)‡ Transition zone§ | | | |
|---|---|---|---|---|---|
| Entry | AR | IN | KY | NC | OK |
| 'DALZ 0102' | 85.0 a# | 34.4 a | 56.7 a | 55.7 a | 44.2 a |
| 'Zorro' | 84.3 a | 32.2 a | 30.0 c | 73.5 a | 46.7 a |
| Himeno | 61.0 a | 28.3 a | 46.7 a | 60.1 a | 37.5 a |
| Emerald | 69.0 a | 28.9 a | 45.7 b | 58.6 a | 30.8 b |
| 'Meyer' | 52.0 b | 25.6 b | 40.0 b | 63.0 a | 30.0 b |

| | Establishment (%)‡ Southeast¶ | | | | |
|---|---|---|---|---|---|
| Entry | FL | MS | SC | TX | Grand Mean |
| 'DALZ 0102' | 25.0 a | 63.3 a | 98.7 a | 10.7 a | 48.6 a |
| 'Zorro' | 21.1 a | 62.8 a | 94.7 a | 10.0 a | 46.4 a |
| Himeno | 22.2 a | 59.2 a | 98.7 a | 4.7 b | 44.7 a |
| Emerald | 18.9 a | 51.3 a | 93.3 a | 4.7 b | 41.5 b |
| 'Meyer' | 17.8 a | 52.9 a | 91.0 b | 5.7 b | 40.8 b |

†Percent divot recovery was rated visually 21 days after divots were made.

‡Percent establishment was estimated visually on a 0 to 100% scale.

§Transition zone: AR, Fayetteville; IN, West Lafayette; KY, Lexington; NC, Raleigh; OK, Stillwater.

¶Southeast zone: FL, Jay; MS, Mississippi State; SC, Florence; TX, Dallas.

#Means in a column followed by the same letter(s) are not significantly different according to Fisher's Protected LSD Test ($p < 0.05$).

Turfgrass quality ratings in the NTEP Test indicated that at the transition zone locations (Fayetteville, Ark., Urbana, Ill., Manhattan, Kans., Lexington, Ky., College Park, Md., Columbia, Mo., Raleigh, N.C., and Stillwater, Okla.) 'DALZ 0102' performed as well ($p\leq0.05$) as 'Meyer', and had significantly superior turfgrass quality than 'Meyer' in KA, MD, and MO (Table 3). The grand mean for turfgrass quality of 'DALZ 0102' (6.4) was superior ($p\leq0.05$) to 'Meyer' (5.2) across all transition zone sites where 'DALZ 0102' will be most competitive in the market. In the southeast region, 'DALZ 0102' had superior turfgrass quality to 'Meyer' at three of six locations: Jay, Fla., and Dallas and College Station, Tex.; quality of 'DALZ 0102' was not different from 'Meyer' at Griffin, Ga., Mississippi State, Miss., or Florence, S.C. In the southwest region, 'DALZ 0102' had superior turfgrass quality to 'Meyer' at both locations: Riverside, Calif. and Las Cruces, N. Mex.

TABLE 3

Turfgrass quality of vegetatively established zoysiagrasses in the NTEP Test over four years.

| | Mean Turfgrass Quality† Transition zone‡ | | | | |
|---|---|---|---|---|---|
| Entry | AR | IL | KS | KY | MD |
| 'Zorro' | 7.2a# | 6.9 a | 6.4 a | 7.5 a | 7.6 a |
| Emerald | 6.9 a | 6.9 a | 7.1 a | 6.6 a | 7.8 a |
| DALZ0102 | 5.8 b | 5.6 b | 7.0 a | 6.6 a | 6.8 ab |
| Himeno | 6.0 b | 5.6 b | 4.7 bc | 7.5 a | 7.0 a |
| 'Meyer' | 5.6 b | 4.8 c | 4.0 c | 7.8 a | 5.3 c |

| | Mean Turfgrass Quality† Transition zone‡ | | | | Southeast§ |
|---|---|---|---|---|---|
| Entry | MO | NC | OK | Grand Mean | FL |
| 'Zorro' | 4.9 a | 6.7 a | 7.5 a | 6.8 a | 6.9 a |
| Emerald | 5.5 a | 6.7 a | 7.2 a | 6.8 a | 6.9 a |
| DALZ0102 | 5.4 a | 6.0 a | 6.7 b | 6.2 b | 6.7 a |
| Himeno | 5.3 a | 6.1 a | 6.5 b | 6.1 b | 6.2 b |
| 'Meyer' | 3.8 b | 5.8 a | 6.1c | 5.4 c | 5.4 c |

| | Mean Turfgrass Quality† Southeast§ | | | | |
|---|---|---|---|---|---|
| Entry | GA | MS | SC | TX1 | TX2 |
| 'Zorro' | 7.5 a | 7.2 a | 7.7 a | 5.8 a | 4.8 a |
| Emerald | 7.3 a | 7.3 a | 7.5 a | 5.1 a | 4.0 b |
| DALZ0102 | 6.7 b | 6.1 c | 6.9 b | 4.9 b | 4.7 a |
| Himeno | 7.3 a | 5.6 d | 7.4 a | 4.2 c | 4.6 a |
| 'Meyer' | 6.5 b | 6.1 c | 6.7 b | 3.4 de | 3.7 b |

| | Mean Turfgrass Quality† | | | |
|---|---|---|---|---|
| | Southeast§ | Southwest¶ | | |
| Entry | Grand Mean | CA | NM | Grand Mean |
| 'Zorro' | 6.9 a | 5.3 a | 6.0 a | 5.7 a |
| Emerald | 6.7 a | 5.0 a | 5.7 a | 5.4 a |
| DALZ0102 | 6.2 c | 5.0 a | 5.3 b | 5.2 b |
| Himeno | 6.1 c | 3.3 d | 5.0 b | 4.4 d |
| 'Meyer' | 5.6 e | 4.0 c | 4.4 c | 4.7 c |

†Turf quality was rated on a 1 to 9 scale where 1 = undesirable quality, 5 = minimum acceptable quality; and 9 = optimum quality.

‡Transition zone: AR, Fayetteville; IL, Carbondale; KS, Manhattan; KY, Lexington; MD, College Park; MO, Columbia; NC, Raleigh; OK, Stillwater.

§Southeast: FL, Jay; GA, Griffin; MS, Mississippi State; NC, Raleigh; SC, Florence; TX1, Dallas; TX2, College Station.

¶Southwest: CA, Riverside; NM, Las Cruces.

#Means in a column followed by the same letter(s) are not significantly different according to Fisher's Protected LSD Test ($p < 0.05$).

Fall color retention generally is a preferred trait in turfgrass, adding aesthetic value. In the 2002 NTEP Test, fall color was rated for five years during the September to December time period (Table 4). Some fall color values in Table 4 are averages of several ratings while other locations rated fall color only once per year. When averaged over the five years of the study, no differences ($p<0.05$) in fall color were observed in 23 of the 31 location-months. 'DALZ 0102' was greener than 'Meyer' at seven of the 31 location-months (IL, KS, NC, MS, TX1, TX2, CA), and 'Meyer' was superior to 'DALZ 0102' at only one of the 31 location-months (IN). During the same evaluation period, 'DALZ 0102' was found to be inferior to *Z. matrella* cultivars for fall color retention, but early fall dormancy is associated with loss of color and is directly related to better freezing tolerance (Fry and Huang, 2004).

TABLE 4

Fall color of vegetatively propagated zoysiagrasses in the NTEP Test over five years.

| | Mean Fall Color† | | | | | |
|---|---|---|---|---|---|---|
| | Transition zone‡ | | | | | |
| Entry | IL | KS | IN | MD | MO | NC |
| DALZ0102 | 6.2ab# | 5.0 a | 4.3 b | 5.7 b | 4.0 b | 6.4 a |
| Emerald | 7.2 a | 5.8 a | 6.3 a | 6.7 a | 5.7 a | 6.5 a |
| Himeno | 4.7 b | 2.7 d | 6.3 a | 5.0 c | 5.3 a | 5.9 a |
| 'Meyer' | 1.8 d | 2.0 d | 6.0 a | 5.3 bc | 4.3 ab | 5.3 b |
| 'Zorro' | 7.8 a | 5.7 a | 3.7 b | 7.3 a | 6.2 a | 5.3 b |

| | Mean Fall Color† | | | | | |
|---|---|---|---|---|---|---|
| | Transition zone‡ | | | | | |
| | | Grand | Southeast§ | | | |
| Entry | OK | Mean | FL | GA | MS | SC |
| DALZ0102 | 4.9 a | 5.2 ab | 4.5 a | 4.3 c | 4.6 a | 7.1 a |
| Emerald | 5.7 a | 6.3 a | 5.6 a | 7.2 a | 5.0 a | 8.0 a |
| Himeno | 5.8 a | 5.1 b | 4.6 a | 3.7 c | 3.8 b | 6.5 a |
| 'Meyer' | 5.7 a | 4.3 b | 4.6 a | 3.8 c | 4.1 b | 6.6 a |
| 'Zorro' | 5.8 a | 6.0 a | 4.8 a | 6.8 a | 5.1 a | 7.7 a |

| | Mean Fall Color† | | | | | |
|---|---|---|---|---|---|---|
| | Southeast§ | | | Southwest | | |
| Entry | TX1 | TX2 | Grand Mean | CA | NM | Grand Mean |
| DALZ0102 | 5.8 a | 5.3 a | 5.3 ab | 4.0 a | 4.8 ab | 4.4 a |
| Emerald | 6.3 a | 4.7 a | 6.1 a | 4.5 a | 5.4 a | 5.0 a |
| Himeno | 5.1 b | 2.7 b | 4.4 c | . | 4.9 a | 4.9 a |
| 'Meyer' | 4.6 c | 3.3 b | 4.5 bc | 2.2 c | 5.2 a | 3.7 a |
| 'Zorro' | 6.3 a | 4.3 a | 5.8 a | 4.8 a | 5.1 a | 5.0 a |

†Fall color was rated on a scale of 1 to 9 where 1 = straw brown and 9 = dark green. Some locations rated fall color several times per year while other locations rated only once per year. Values in the table indicated averages over a period of five years of evaluation at all locations.
‡Transition zone: IL, Carbondale; KS, Manhattan; IN, West Lafayette; MD, College Park; MO, Columbia; NC, Raleigh; OK, Stillwater.
§Southeast: FL, Jay; GA, Griffin; MS, Mississippi State; SC, Florence; TX1, Dallas; TX2, College Station.
¶Southwest: CA, Riverside; NM, Las Cruces.
#Means in a column followed by the same letter(s) are not significantly different according to Fisher's Protected LSD Test ($p < 0.05$).

Spring density ratings, indicating earlier and faster spring growth, for 'DALZ 0102' were significantly better than those for 'Meyer' in the NTEP Test at three of five locations, Jay, Fla., Las Cruces, N. Mex., and Dallas, Tex. (Table 5). Likewise, autumn density ratings for 'DALZ 0102' were significantly better than 'Meyer' at four of six locations, including Jay, Fla., Las Cruces, N. Mex., and Dallas, Tex. 'Meyer' was never significantly better than 'DALZ 0102' in spring or autumn density ratings.

TABLE 5

Shoot Density of vegetatively established zoysiagrasses in the NTEP Test over four years.

| | Mean Density† | | | | | |
|---|---|---|---|---|---|---|
| | Spring | | | | | |
| Entry | FL‡ | NC | NM | OK | TX1 | Grand Mean |
| 'Zorro' | 6.8 a§ | 8.3 a | 9.0 a | 8.0 a | 6.0 a | 7.0 a |
| DALZ0102 | 6.7 a | 7.7 a | 9.0 a | 7.0b | 6.1 a | 6.9 a |
| Emerald | 6.8 a | 8.3 a | 8.0 d | 7.7 a | 5.4 a | 6.8 a |
| Himeno | 6.3 a | 7.7 a | 9.0 a | 6.7 b | 4.4 b | 6.3 a |
| 'Meyer' | 5.7 b | 7.3 a | 7.0 g | 6.3 b | 2.9 c | 5.8 b |

TABLE 5-continued

Shoot Density of vegetatively established zoysiagrasses in the NTEP Test over four years.

| | Mean Density† | | | | | |
|---|---|---|---|---|---|---|
| | Fall | | | | | |
| Entry | AR | FL | NC | NM | TX1 | TX2 | Grand Mean |
| 'Zorro' | 7.3 a | 8.3 a | 7.0 a | 9.0 a | 7.8 a | 8.3 a | 8.0 a |
| DALZ0102 | 5.0 b | 8.0 a | 6.7 a | 9.0 a | 7.7 a | 7.3 a | 7.3 a |
| Emerald | 6.3 a | 8.1 a | 7.3 a | 9.0 a | 6.5 a | 7.0 a | 7.4 a |
| Himeno | 4.3 c | 7.8 a | 7.0 a | 8.3 c | 6.2 ab | 6.7 a | 6.7 b |
| 'Meyer' | 5.7 b | 7.0 b | 6.3 a | 8.0 d | 4.6 bc | 5.7 b | 6.2 c |

†Turf density was rated on a scale of 1 to 9 where 1 = bare ground and 9 = the greatest number of plants per unit area.
‡FL, Jay; NC, Raleigh; NM, Las Cruces; OK, Stillwater; TX1, Dallas; AR, Fayetteville; TX2, College Station.
§Means in a column followed by the same letter(s) are not significantly different according to Fisher's Protected LSD Test ($p < 0.05$).

Environmental Stresses—Patton and Reicher (2007) reported no significant difference between 'DALZ 0102' and 'Meyer' for spring green up, an indicator of winter injury. 'DALZ 0102' had more ($p<0.05$) winter injury (9%) than 'Meyer' (0%), and both were superior to a number of zoysiagrass cultivars in each year, including 'Zorro', which exhibited 18% winter injury in one year and 28% two years later, 'El Toro', *Z. japonica*, at 37% injury in one year and 54% in the following year, and 'Palisades', which exhibited 31% winter injury one year and 61% in the following year. These zoysiagrass cultivars also were exposed to controlled freezing temperatures in a cold stress simulator and the authors reported that 'Meyer' had a lower $LT_{50}$ value of −11.5° C. as compared with Cavalier (−10.3° C.), 'DALZ 0102' (−10.2° C.), 'Zorro' (−9° C.), and Diamond (−8.4° C.).

Okeyo et al. (2011b) evaluated the freezing tolerance of 'DALZ 0102' and 'Meyer', along with other experimental zoysiagrasses. The grasses were sampled by taking 6-cm diameter cores from the field in February and December, and exposed to a regimen of temperatures in the freezer. 'DALZ 0102' and 'Meyer' did not differ significantly for $LT_{50}$ lethal temperatures. When 'DALZ 0102' and 'Meyer' rhizomes were sampled from the field in Manhattan, Kans. and exposed to controlled freezing temperatures in February, the greatest decline in rhizome survival in both grasses occurred between −13 and −15° C. (Zhang and Fry, 2007). 'Meyer' had some rhizome survival at −17° C., whereas 'DALZ 0102' exhibited no recovery growth after exposure to −15° C.

In general, *Z. japonica* has average to poor shade tolerance (Fry and Huang, 2004), and 'Meyer' was found to possess relatively poor shade tolerance among other *Z. japonica* cultivars in a 3-year study in Texas (Wherley et al., 2011). Wherley et al. established 5 $cm^2$ round plugs under 90% live oak tree (*Quercus viriginiana* Mill.) shade and maintained under low-maintenance conditions. Over three seasons, numerous developmental parameters including lateral spread and visual quality were evaluated monthly. 'DALZ 0102' ranked in the top statistical grouping of the 27 medium and medium-coarse-textured entries for lateral spread, and had improved quality relative to 'Meyer', which consistently ranked near the bottom. By the end of the 3-year study, 'DALZ 0102' plugs exhibited a 17-fold increase in diameter in comparison to the original size plug, whereas 'Meyer' had increased in size by only 4-fold. At the conclusion of the study, a turf performance index (TPI) was developed, which represented the total number of times an entry ranked within the top statistical grouping, considering all parameters and years. Based on this 3-year ranking, 'DALZ 0102' ranked in the top statistical grouping 44 times compared to 19 times for 'Meyer'. This ranked 'DALZ 0102' at 14 of 27 entries, compared to 'Meyer', which ranked 26 of 27. While the shade tolerance in 'DALZ 0102' is average relative to other medium and medium-coarse textured *zoysia* cultivars, it was superior to 'Meyer' in this study.

Pests—Bluegrass billbug (*Sphenophorus parvulus* Gyllenhal) adults lay eggs on the leaf sheaths of zoysiagrass and can be a pest for this warm-season grass as well. Larvae hatch and then tunnel into stems ultimately resulting in circular necrotic areas in the turf of up to 5 cm in diameter. When evaluated in the field experiencing natural infestation in Manhattan, Kans. over a 2-year period, 'Meyer' exhibited 17 to 38% plot injury from bluegrass billbug infestation, whereas 'DALZ 0102' had no injury (Fry and Cloyd, 2011). Zoysiagrass mite (*Eriophyes zoysiae* Baker, Kono, and O'Neill) infestations can result in twisted shoot tips as new leaves partially unroll and emerge from the whirl of older leaves, resulting in what is referred to as a "buggy whip" symptom. It is a nuisance pest since it contributes to the loss of aesthetic value and further can weaken the turf rendering it vulnerable to loss from other stresses. Greenhouse testing showed a high potential for resistance to the mite in Emerald and 'Royal' zoysiagrass while most cultivars including 'Meyer' are susceptible (Reinert et al., 1993). In a separate greenhouse experiment at Dallas, Tex. under natural mite infestation, 'DALZ 0102' showed a light infestation of mites (4.9% infested terminal shoots per 6.35 $cm^2$ plant cell plug) with 28% of the plugs in 18-cell tray expressing symptoms. Emerald, which had expressed resistance in the earlier study (Reinert et al., 1993), exhibited resistance in the present study. In contrast, more than 20% of the terminals in a 6.35 $cm^2$ plant cell plug of 'Meyer' expressed symptoms and 100% of the plugs in an 18-cell tray were infested.

Large patch (*Rhizoctonia solani* Kühn) is the most significant disease problem on zoysiagrass, and typically occurs during spring and autumn in the transition zone. Affected turf develops circular patches of necrotic leaf tissue that can reach up to several meters in diameter. 'DALZ 0102' was evaluated for large patch susceptibility in Manhattan, Kans. In both field and growth chamber studies, large patch susceptibility of 'DALZ 0102' did not differ from 'Meyer' (Obasa and Kennelly, 2012). Similarly, ratings were observed on plots planted at Stillwater, Okla., Raleigh, N.C., and at Purdue, Ind. with no difference between 'DALZ 0102' and 'Meyer' for their response to large patch (NTEP, 2007).

Take-all patch [*Gaeumannomyces graminis* var. *graminis* (Sacc.) Arx & D. L. Olivier] is a disease of warm-season grasses that infects the root system. Initially, the affected turf becomes wilted and yellow, followed by the development of thin, bare areas as the plant canopy dies. Since the roots that anchor the sod to the soil die, the turf can usually be pulled from the soil quite easily as a result of the infection. When evaluated in the NTEP Test for take-all patch resistance at Dallas, Tex., 'DALZ 0102' received a superior ($p<0.05$) rating of 8.7 (0 to 9 scale; 9=no disease) compared to 'Meyer', which received a rating of 3.7 (NTEP, 2007).

Seedhead Production—Even vegetatively propagated zoysiagrasses can produce significant numbers of seedheads, which are generally considered unsightly and reduce turf quality. 'DALZ 0102' had a superior ($p<0.05$) seedhead rating (fewer seedheads) compared to 'Meyer' at four of seven locations when averaged over four years (Table 6).

TABLE 6

Seedhead ratings for vegetatively established zoysiagrasses in the NTEP Test over four years.

| | Mean Seedheads† | | | | | |
|---|---|---|---|---|---|---|
| | Transition zone‡ | | | | | |
| | | | | Grand | Southeast§ | |
| Entry | AR | IL | OK | Mean | MS | SC |
| DALZ0102 | 8.8 a# | 9.0 a | 8.7 a | 8.8 a | 8.2 a | 9.0 a |
| Emerald | 9.0 a | 9.0 a | 8.0 b | 8.7 a | 7.5 a | 8.2 a |
| Himeno | 6.3 c | 9.0 a | 9.0 a | 8.1 a | 8.3 a | 8.8 a |
| 'Meyer' | 6.3 c | 9.0 a | 6.3 de | 7.2 a | 3.3 d | 8.5 a |
| 'Zorro' | 8.8 a | 9.0 a | 8.0 b | 8.6 a | 6.7 b | 8.8 a |

| | Mean Seedheads† | | | | |
|---|---|---|---|---|---|
| | Southeast§ | | | | |
| | | | Grand | Southwes¶ | Total |
| Entry | FL | TX2 | Mean | NM | Mean |
| DALZ0102 | 9.0 a | 5.7 e | 8.0 a | 7.7 a | 8.2 a |
| Emerald | 9.0 a | 6.3 d | 7.8 a | 8.0 a | 8.2 a |
| Himeno | 9.0 a | 7.7 b | 8.5 a | 7.7 a | 8.1 a |
| 'Meyer' | 8.2 a | 2.3 i | 5.6 b | 7.7 a | 6.8 b |
| 'Zorro' | 9.0 a | 9.0 a | 8.4 a | 7.7 a | 8.2 a |

†Seedheads were rated on a 1 to 9 scale, where 1= maximum amount of seedheads, and 9 = no seedheads present.
‡Transition zone: AR, Fayetteville; IL, Carbondale; OK, Stillwater.
§Southeast: MS, Mississippi State; SC, Florence; FL: Jay, TX2, College Station.
¶Southwest: NM, Las Cruces.
#Means in a column followed by the same letter(s) are not significantly different according to Fisher's Protected LSD Test ($p < 0.05$).

REFERENCES

Dunn, J. H., and K. Diesburg. 2004. Turf Management in the Transition Zone. John Wiley & Sons, Hoboken, N.J.

Engelke, M. C., and S. J. Anderson. 2003. Zoysiagrasses, p. 271-286. In M. D. Casler and R. R. Duncan (eds.) Turfgrass biology, genetics, and breeding. John Wiley & Sons, Hoboken, N.J.

Forbes, I., 1952. Chromosome numbers and hybrids in *Zoysia*. Agron. J. 44: 147-151.

Fry, J. and R. Cloyd. 2011. Zoysiagrass genotypes differ in susceptibility to the bluegrass billbug, *Sphenophorus parvulus*. HortScience 46:1314-1316.

Fry, J. and P. Dernoeden. 1987. Growth of zoysiagrass from vegetative plugs in response to fertilizers. J. Am. Soc. Hort. Sci. 112:286-289.

Fry, J. and B. Huang. 2004. Applied Turfgrass Science and Physiology. John Wiley & Sons, Hoboken, N.J.

Grau, F. V. and A. M. Radko. 1951. 'Meyer' (Z-52) zoysiagrass. USGA J. of Turf Management 4(6):30-31.

Green, D., J. Fry, J. Pair, and N. Tisserat. 1993. Pathogenicity of *Rhizoctonia solani* AG-2-2 and *Ophiosphaerella herpotricha* on zoysigrass. Plant Dis. 77:1040-1044.

Halsey, H. 1956. The *zoysia* lawn grasses. Nat. Hort. Mag. 35:152-161.

Hong, K. H. and D. Y. Yeam. 1985. Studies on interspecific hybridization in Korean lawn grasses (*Zoysia* spp.). J. Korean Soc. Hort. Sci. 26:169-178.

Marcum, K. B., M. C. Engelke, S. J. Morton, and R. H. White. 1995. Rooting characteristics and associated drought resistance of zoysiagrasses. Agron. J. 87: 534-538.

Morris, K. N. and R. C. Shearman. 1999. NTEP turfgrass evaluation guidelines. National Turfgrass Evaluation Program, Beltsville, Md. (ntep.org).

National Turfgrass Evaluation Program. 2007. National zoysiagrass test—2002. Final Report no. 07-11. (ntep.org).

Obasa, K., J. Fry, and M. Kennelly. 2012. Susceptibility of zoysiagrass germplasm to large patch caused by *Rhizoctonia solani*. HortScience. 47: 1252-1256.

Okeyo, D., J. Fry, D. Bremer, A. Chandra. D. Genovesi, and M. Engelke. 2011a. Stolon growth characteristics and establishment rates of zoysiagrass progeny. HortScience 46:113-117.

Okeyo, D., J. Fry, D. Bremer, C. Rajashekar, M. Kennelly, A. Chandra, D. Genovesi, and M. Engelke. 2011b. Freezing tolerance and seasonal color of experimental zoysiagrasses. Crop Sci. 51: 2858-2863.

Patton, A. J. and Z. J. Reicher. 2007. Zoysiagrass species and genotypes differ in their winter injury and freeze tolerance. Crop Sci. 47: 1619-1627.

Patton, A. J., J. Volenec, and Z. Reicher. 2007. Stolon growth and dry matter partitioning explain differences in zoysiagrass establishment rates. Crop Sci. 47:1237-1245.

Reinert, J. A., M. C. Engelke, and S. J. Morton. 1993. Zoysiagrass resistance to the zoysiagrass mite, *Eriophyes zoysiae* (Acari:*Eriopyidae*). Int. Turfgrass Soc. Res. J. 7: 349-352.

Wherley, B. G., P. Skulkaew, A. Chandra, A. D. Genovesi, and M. C. Engelke. 2011. Low-input performance of zoysiagrass (*Zoysia* spp.) cultivars maintained under dense tree shade. HortScience 46: 1033-1037.

Yaneshita, M., S. Kaneko, and T. Sasakuma, 1999. Allotetraploidy of *Zoysia* species with 2n=40 based on a RFLP genetic map. Theor. Appl. Genet. 98: 751-756.

Zhang, Q. and J. Fry. 2007. Preliminary evaluation of freezing tolerance of Meyer and DALZ 0102 zoysiagrass. Kansas State Turfgrass Research. Report of Progress 981. KSU Agricultural Experiment Station and Cooperative Extension Service.

What is claimed is:

1. A new and distinct variety of zoysiagrass called 'DALZ 0102' as shown and described herein.

* * * * *